US007014461B2

(12) United States Patent
Weinstein

(10) Patent No.: US 7,014,461 B2
(45) Date of Patent: Mar. 21, 2006

(54) HARD TISSUE SURFACE GEOMETRY DETERMINATION

(75) Inventor: Uriel Weinstein, Mazkeret-Batya (IL)

(73) Assignee: Tactile Technologies LLC, Las Vegas, NV (US)

( * ) Notice: Subject to any disclaimer, the term of this patent is extended or adjusted under 35 U.S.C. 154(b) by 250 days.

(21) Appl. No.: 10/350,288

(22) Filed: Jan. 23, 2003

(65) Prior Publication Data
US 2004/0146830 A1 Jul. 29, 2004

(51) Int. Cl.
A61C 3/02 (2006.01)

(52) U.S. Cl. .............................. 433/76; 433/72; 33/553

(58) Field of Classification Search ................ 433/76, 433/72, 75; 33/553–554, 561.1
See application file for complete search history.

(56) References Cited

U.S. PATENT DOCUMENTS

| 3,861,049 A | * | 1/1975 | Muller .......................... 33/562 |
| 4,998,881 A | * | 3/1991 | Lauks .......................... 433/173 |
| 5,133,660 A | | 7/1992 | Fenick |
| 5,163,940 A | | 11/1992 | Bourque |
| 5,176,516 A | * | 1/1993 | Koizumi ...................... 433/72 |
| 5,257,184 A | | 10/1993 | Mushabac |
| 5,343,391 A | | 8/1994 | Mushabac |
| 5,562,448 A | | 10/1996 | Mushabac |
| 5,613,852 A | | 3/1997 | Bavitz |
| 5,688,283 A | | 11/1997 | Knapp |
| 5,725,376 A | * | 3/1998 | Poirier ........................ 433/172 |
| 5,800,168 A | | 9/1998 | Cascione et al. |
| 5,860,806 A | * | 1/1999 | Pranitis et al. ................ 433/80 |
| 5,865,769 A | * | 2/1999 | Case et al. ................... 600/587 |
| 5,967,777 A | | 10/1999 | Klein et al. |
| 6,062,856 A | | 5/2000 | Sussman |
| 6,319,006 B1 | | 11/2001 | Scherer et al. |
| 6,402,707 B1 | * | 6/2002 | Ernst ........................... 600/590 |
| 6,491,700 B1 | | 12/2002 | Lavallee et al. |
| 2001/0053510 A1 | | 12/2001 | Ranalli |

FOREIGN PATENT DOCUMENTS

GB    2 252 911    8/1992

OTHER PUBLICATIONS

Brief, J. et al.; "Computer-guided Insertion of Dental Implants—a Clinical Evaluation;" International Congress Series 1230; 2001; pp. 739-747.
Lobregt, S. et al.; "Dental Implant Surgery: Planning and Guidance;" MEDICAMUNDI; vol. 45; No. 4; Nov. 2001; pp. 30-35.
Shapira, L.; "Image Guided Implantology—Real-Time Guidance of Dental Implant Surgery in the Operative Field Using CT-Scan Image;" 8th Computed Maxillofacial Imaging Congress; Part of the CARS 2002 Computer Assisted Radiology and Surgery, 16th International Congress and Exhibition; Jun. 26-29, 2002; 4 pages.
TEAM Surgery to Recovery/Resultz Innovative Healthcare Supplies & Service; Anthrex Transtibial ACL/PCL System Adapteur Multi Function Drill Guide System; 1 page; Retrieved from the internet on Dec. 22, 2002 <http://www.teamresultz.com/team/surg/knee/kn009.html>.

* cited by examiner

Primary Examiner—John J Wilson
(74) Attorney, Agent, or Firm—Fenster & Co

(57) ABSTRACT

Apparatus for measuring a surface geometry of hard tissue covered by a layer of soft tissue, including a plurality of elements each having a tip adapted to penetrate said soft tissue and not substantially penetrate said hard tissue; a frame supporting movement of said elements, each along a path, such that a plurality of said tips, when positioned along the paths, define a surface; and at least one position sensor which generates a signal indicative of a tip position of at least one of said elements.

81 Claims, 11 Drawing Sheets

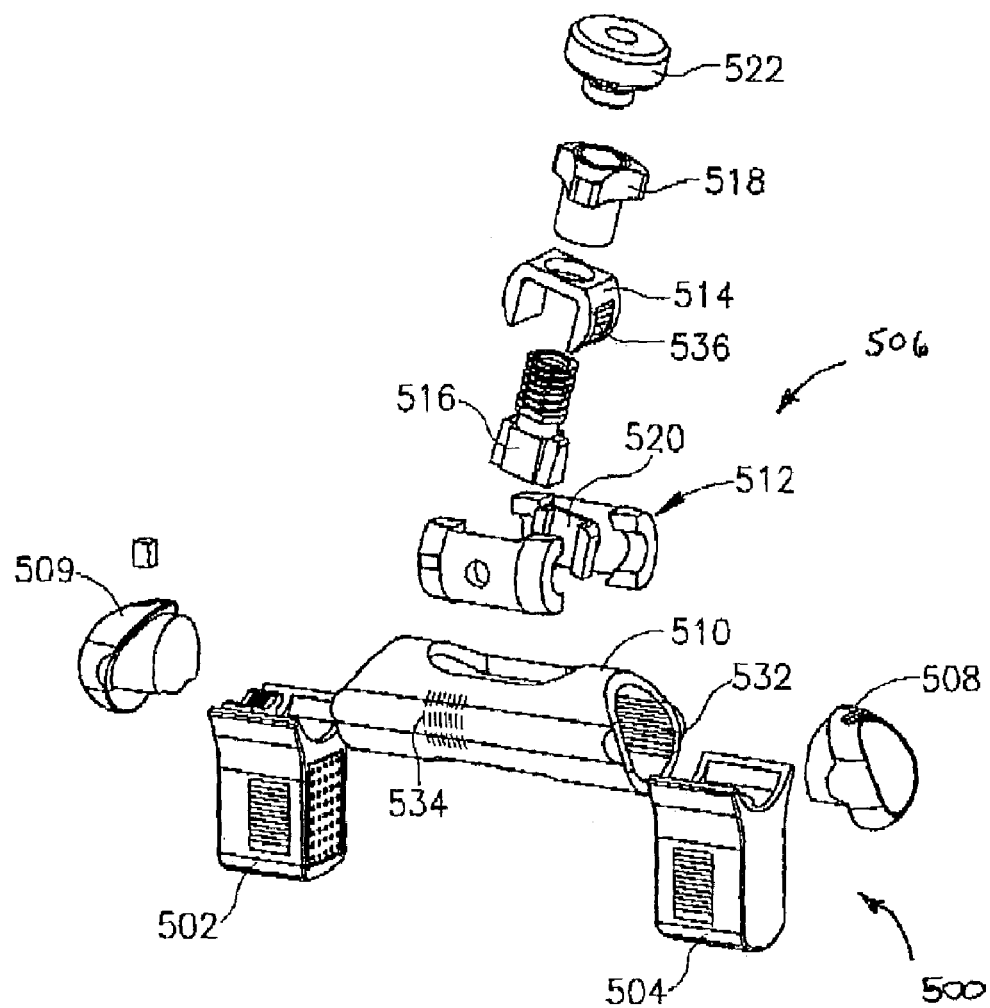
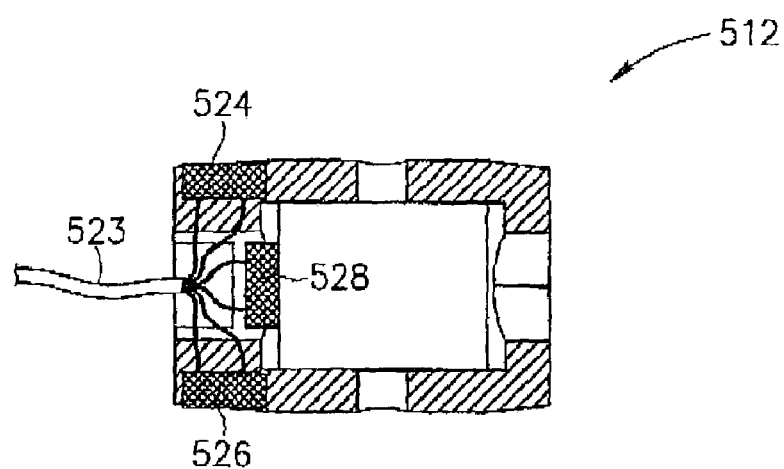
FIG.5A
FIG.5B

US 7,014,461 B2

HARD TISSUE SURFACE GEOMETRY DETERMINATION

FIELD OF THE INVENTION

The present invention relates to the measurement of surface geometries, for example, of dental and bone tissues.

BACKGROUND OF THE INVENTION

There are many applications where knowing the surface structure or internal structure of hard tissue is desirable. A typical solution, especially if the hard tissue is underlying soft tissue as is the case in dental care, is to obtain X-Ray CT images of the hard tissue U.S. Pat. No. 5,562,448 to Mushabac, the disclosure of which is incorporated herein by reference, describes an array of sensors which are slid over one or more teeth, to determine its surface structure. However, the position of the array must be determined for each measurement of the array. This patent also describes a point-by-point digitizing of jaw-bone surface by penetrating overlying soft tissue to the bone with a sharp probe, multiple times, again, requiring position determination for each point digitization. The multiple position determination may cause registration and/or other accuracy problems.

In dental tooth implantation other than by the method of U.S. Pat. No. 5,562,448, it is common practice to peel the soft gum tissue off of the jaw bone, in order to better visualize the jaw bone surface geometry.

While common practice is to determine the drilling direction by feel, it has been suggested to mount a surgical stent (template) on the jaw bone, to guide the drilling. The stent may be manufactured, for example, using CAD/CAM techniques and based on CT images of the jaw.

U.S. Pat. No. 5,163,940 to Bourque, the disclosure of which is incorporated herein by reference describes a measurement device for making a measurement of a joint portion.

SUMMARY OF THE INVENTION

An aspect of some embodiments of the invention relates to apparatus for determining surface geometry of a hard tissue underlying soft tissue. In an exemplary embodiment of the invention, a plurality of pins or other tipped elements are advanced so that the tips penetrate the soft tissue and substantially do not penetrate, or penetrate by a known amount, the hard tissue. The surface may be reconstructed by knowing the relative positions of the tips in an exemplary embodiment of the invention, the pins arc coupled together so that their relative position, in at least one or two dimensions is known, for example, the pins each having a fixed channel along which substantially only motion along the axis of the pin is possible.

In an exemplary embodiment of the invention, the apparatus is designed as a dental stent for simultaneous measurement of two sides and at least part of a top of a jaw bone where a tooth is to be implanted In an exemplary embodiment of the invention, a drilling direction, position and/or depth in the jaw is estimated as a function of the determined surface geometry.

Optionally, the dental stent includes one or more locking pins to lock the stent to a jaw bone.

In an exemplary embodiment of the invention, the apparatus includes a built-in mechanism which determine the axial positions of the pins, and thus of the tips.

Optionally, the apparatus includes a pin advancer and/or retractor.

In an exemplary embodiment of the invention, the surface geometry is used as an input for a dental surgery planning system and/or drill guide. Alternatively or additionally, the surface geometry and/or tip position is used to control and/or monitor a drilling process. Optionally, the apparatus includes a drill guide whose orientation is controlled and/or monitored by the apparatus, responsive to the tip position.

There is thus provided in accordance with an exemplary embodiment of the invention, apparatus for measuring a surface geometry of hard tissue covered by a layer of soft tissue, comprising:

(a) a plurality of elements each having a tip adapted to penetrate said soft tissue and not substantially penetrate said hard tissue;

(b) a frame supporting movement of said elements, each along a path, such that a plurality of said tips, when positioned along the paths, define a surface; and (c) at least one position sensor which generates a signal indicative of a tip position of at least one of said elements. Optionally, said path comprises a path along an axis of said elements.

Alternatively or additionally, said elements are elongate.

In an exemplary embodiment of the invention, said frame comprises two substantially oppositely facing panels, each of which panels supports a plurality of said elements. Optionally, said frame comprises at least one upper panel supporting a plurality of said elements. Alternatively or additionally, said frame comprises at least one upper panel supporting at least one fixed soft tissue penetration element. Alternatively or additionally, said tips are adapted to measure at least three sides of a shape generally corresponding to a rectangle, while mounted in said frame. Alternatively or additionally, said elements are arranged as a first set perpendicular to one plane, a second set generally facing said first plane and a third set oblique to said first and second sets.

In an exemplary embodiment of the invention, at least some of said plurality of elements are arranged in two dimensions, with at least three elements in each of two orthogonal directions.

In an exemplary embodiment of the invention, said frame is adapted for disassembly.

In an exemplary embodiment of the invention, said plurality of elements comprises at least 10 elements. Optionally, said plurality of elements comprises at least 30 elements.

In an exemplary embodiment of the invention, the apparatus is sized and has a geometry adapted for a dental application of measuring a surface of a jaw bone based on axial positions of said tips.

In an exemplary embodiment of the invention, said hard tissue comprises cortical bone tissue.

Optionally, said tips have a density of at least one tip per nine square millimeters. Optionally, said tips have a density of at least one tip per square millimeter.

In an exemplary embodiment of the invention, said frame substantially allows only motion of each of said elements, along an axis of the element. Optionally, said frame is limited to non-axial motion to within a tolerance of less than 10% of a pitch of said elements. Optionally, said frame allows only axial motion of said elements, within a tolerance of less than 5% of a pitch of said elements to non-axial motion of said tips.

In an exemplary embodiment of the invention, said tips are made sharp enough to penetrate soft tissue bat not so sharp that they penetrate cortical bone under an application force of under 50 gas.

In an exemplary embodiment of the invention, said tips include a bone stop which prevents entry of the elements into bone tissue past said a predetermined distance.

Optionally, said at least one encoder comprises a single encoder common to multiple elements. Optionally, said at least one encoder comprises-an imaging encoder.

Alternatively, said at least one encoder comprises at least one encoder per element. Optionally, said at least one encoder comprises an optical encoder reading a position marking off of an element. Alternatively or additionally, said at least one encoder comprises a magnetic encoder reading a position marking off of an element. Alternatively or additionally, said at least one encoder comprises a resistance encoder reading a resistance of an element. Alternatively or additionally, said at least one encoder comprises a capacitance encoder reading a capacitance of an element. Alternatively or additionally, said at least one encoder comprises a force encoder reading a compression of a spring attached to an element.

In an exemplary embodiment of the invention, said at least one encoder has a precision of better than 0.5 mm. Optionally, said at least one encoder has a precision of better than 0.2 mm.

In an exemplary embodiment of the invention, said at least one encoder is integral to said frame.

In an exemplary embodiment of the invention, said at least one encoder is separate from said frame. Optionally, the apparatus comprises a holder for at least part of said frame in which said at least one encoder is integrated.

In an exemplary embodiment of the invention, the apparatus comprises an element advance mechanism operative to simultaneously advance a plurality of said elements through said soft tissue at a same time. Optionally, said element advance mechanism is adapted to apply a force limited to prevent inadvertent penetration of said hard tissue. Alternatively or additionally, said element advance mechanism comprises a pneumatic advance mechanism. Optionally, the apparatus comprises a pneumatic channel for each of said elements. Optionally, said advance mechanism is operable as an element retractor.

In an exemplary embodiment of the invention, the apparatus comprises at least one position lock for at least one of said elements. Optionally, said position lock comprises a friction lock defined by a panel perpendicular to an axial motion direction of said elements.

In an exemplary embodiment of the invention, the apparatus comprises a source of adhesive adapted to provide adhesive to lock said elements to said frame.

In an exemplary embodiment of the invention, the apparatus comprises at least one support adapted to lock said frame relative to at least one of said soft tissue and said hard tissue.

In an exemplary embodiment of the invention, the apparatus comprises a drill guide. Optionally, said drill guide is adapted to guide a standard dental drill bit. Optionally, said drill guide is adapted to limit a depth of penetration of said drill bit. Alternatively or additionally, said drill guide is locked to said frame. Optionally, said drill guide is adjustable in at least two degrees of freedom of position and orientation prior to being locked to said frame. Optionally, said drill guide is adjustable in at least three degrees of freedom of position and orientation prior to being locked to said frame. Alternatively or additionally, the apparatus comprises at least one encoder adapted to measure at least one of said degrees of freedom.

In an exemplary embodiment of the invention, said drill guide comprises at least one penetration limitation sleeve having a selectable offset from said frame. Optionally, said at least one penetration limitation sleeve comprises a plurality of sleeves each having a different offset.

In an exemplary embodiment of the invention, said encoder comprises a data output. Optionally, said data output is wireless. Alternatively or additionally, the apparatus comprises a three dimensional display system to which said data output is attached, which display system is adapted to display an indication of said surface. Optionally, said display system overlays said surface on a three dimensional representation of said hard tissue. Alternatively or additionally, the apparatus comprises a controller configured to resister said surface to said representation. Alternatively or additionally, said display system generates alerts responsive to an undesirable spatial position of a tool relative to said surface. Alternatively or additionally, said display system generates an indication of at least one of a position and orientation of a drill guide mounted on said frame. Optionally, said indication comprises indication of a projected drill bore.

In an exemplary embodiment of the invention, the apparatus comprises a computerized manufacturing system to which said data output is attached, for manufacture of a drill guide for said hard tissue.

In an exemplary embodiment of the invention, the apparatus comprises a plurality of elements having tips adapted to not penetrate soft tissue.

There is also provided in accordance with an exemplary embodiment of the invention, a method of measuring the surface of a hard tissue underlying a soft tissue, comprising:

(a) inserting a plurality of different sharp elements through said soft tissue to a surface of said hard tissue;

(b) determining at least relative positions of tips of said sharp elements; and (c) reconstructing a map of said surface of said hard tissue from said at least relative positions. Optionally, the method comprises using said map to guide a drill to said hard tissue. Optionally, the method comprises providing a drill guide for using said map. Optionally, said hard tissue comprises a jaw bone and wherein said soft tissue comprises hard tissue.

In an exemplary embodiment of the invention, the method comprises selecting an offset sleeve for controlling a depth of said drilling. Alternatively or additionally, the method comprises adjusting said drill guide according to said map.

In an exemplary embodiment of the invention, said elements are mounted on two opposing panels of a fame and comprising approximating said panels. Alternatively or additionally, the method comprises registering said map to a previously acquired radiological image of said hard tissue. Alternatively or additionally, the method comprises providing real-time feedback on at least one of a position and orientation of said drill guide.

In an exemplary embodiment of the invention, inserting comprises inserting using a standard dental pneumatic source. Alternatively or additionally, the method comprises removing said elements using a standard dental pneumatic source.

In an exemplary embodiment of the invention, the method comprises removing said elements from said soft tissue prior to said determining. Alternatively, the method comprises removing said elements from said soft tissue after said determining.

In an exemplary embodiment of the invention, the method comprises locking said elements prior to said determining. Alternatively, the method comprises not locking said elements prior to said determining.

There is also provided in accordance with an exemplary embodiment of the invention, a dental surgical stent, comprising:

(a) an active stent portion adapted to fit over a portion of a jaw bone; and (b) at least one visual indicator showing an activation state of said stent.

There is also provided in accordance with an exemplary embodiment of the invention, a dental surgical stent, comprising:

(a) a surgical stent portion adapted for mounting on a jaw; and (b) a drill guide including at least one encoder which generates a signal indicative of at least one of a position and orientation of the drill guide. Optionally, said surgical stent is machined for a particular jaw. Alternatively or additionally, said surgical stent comprises at least one mounting point for said drill guide.

BRIEF DESCRIPTION OF THE DRAWINGS

Non-limiting embodiments of the invention will be described with reference to the following description of exemplary embodiments, in conjunction with the figures. The figures are generally not shown to scale and any measurements are only meant to be exemplary and not necessarily limiting. In the figures, identical structures, elements or parts which appear in more than one figure are preferably labeled with a same or similar number in all the figures in which they appear, in which:

FIGS. 5A–5D are schematic illustrations of a stent including a drill guide, in accordance with an exemplary embodiment of the invention;

DETAILED DESCRIPTION OF EXEMPLARY EMBODIMENTS

Overview of Tooth Implant Problem

Figure 1A:
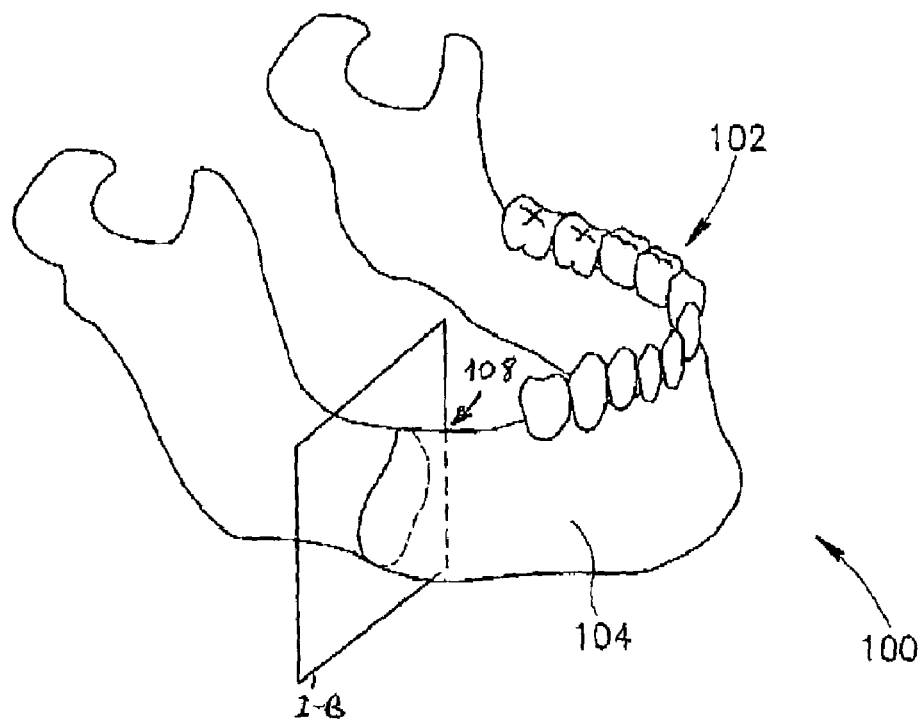
FIGS. 1A and 1B are schematic isometric and a cross-sectional illustration of a jaw bone, showing the various layers thereof.
Figure 1B:
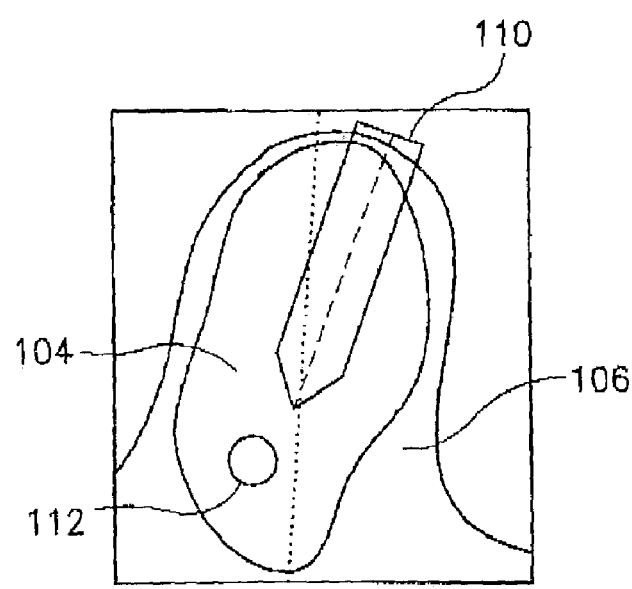

FIGS. 1A and 1B are a schematic isometric and a cross-sectional (along plane I-B of FIG. 1A) illustration of a jaw 100, showing the various layers thereof. A plurality of teeth 102 are embedded in a jaw-bone 104. A layer of soft gum tissue 106 overlays bone 104. If a tooth is missing, for example as in a space 108, the jaw bone may resorb, making later implantation difficult or impossible. In addition, there are esthetic considerations and a danger (if for example a bridge is not provided), that teeth might migrate into space 108. Thus, it is often desirable to implant new teeth instead of the missing teeth. While a tooth may be mounted using a bridge to nearby teeth, it may be desirable for a number of reasons that the tooth be anchored in jawbone 104. A typical procedure is to drill a bore 110 in jaw bone 104 and mount a tooth implant in bore 110. Two main dangers with the drilling are (a) the bore might be too close to the sides of jaw bone 104 (the cortical layer); and (b) the bore might reach to the mandibular nerve 112. In addition, a certain orientation, for mechanical, crown design and/or esthetic reasons is often desirable, so the bore orientation should generally be within certain parameters. These considerations also apply to the upper jaw, in which additional dangers of incorrect placement include causing chronic sinus problems or even penetrating the brain.

It should be noted that once a tooth is lost, the jaw-bone resorbs, typically within 6 months, so a completely new bore must be drilled. Interpretation of CT images, selecting a bore direction and, especially, actually drilling in a correct direction, require considerable expertise, not acquired by most dentists.

Exemplary Stent Embodiment

Figure 2:
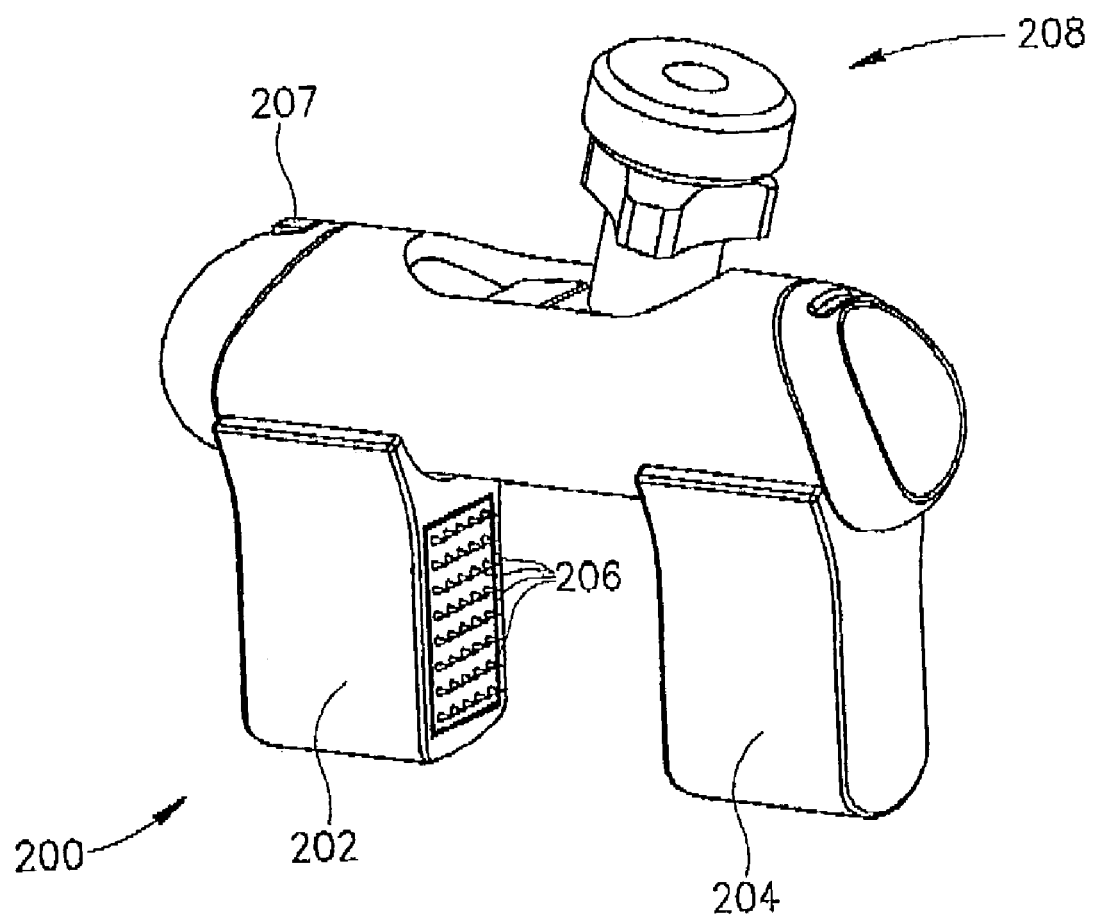
FIG. 2 is a schematic illustration of a stent in accordance with an exemplary embodiment of the invention.

FIG. 2 is a schematic illustration of a stent 200 in accordance with an exemplary embodiment of the invention, in which stent 200 is used to determine the surface geometry of the jawbone underlying space 108. FIG. 1B shows a desired bore direction, which may be determined, for example as a tradeoff between a bore direction aligned with a chewing direction and a bore direction in which the jaw bone is less likely to fracture under the stress of implantation and chewing. Generally, a bore that is centered in the jaw bone is desirable.

In an exemplary embodiment of the invention, stent 200 comprises one or more side panels 202 and 204 which are presented to a side of space 108. A plurality of sharp-tipped pins 206 are advanced from panel 202 so that they pierce soft tissue 1.06 and contact bone 104. The pin tips are designed to not enter bone or to enter it to a substantially small and/or measured amount. Thus, determining the relative positions of the tips of pins 206 can assist in determining the 3D surface geometry of bone 104. Optionally, a drill guide 208 is provided on stent 200. In one embodiment, drill guide 208 is controlled and/or monitored by stent 200, for example to ensure a desired bore angle is provided. In another embodiment, drill guide 208 is fabricated or adjusted based on signals received from stent 200 to indicate the bone geometry and drill guide 208 is mounted on stent 200, which remains on space 108. The pins may be advanced, for example, individually and/or as one or more groups, for example as described below.

In an exemplary embodiment of the invention, stent 200 includes one or more LED or other operating light 207 or display to indicate that the stent is active and/or its operational state.

In an exemplary embodiment of the invention, two panels 202 and 204 are used, so that jaw 100 can be rigidly engaged by stein 200 and measurements made of both sides of the jaw bone. Optionally, one or more locking screws 209 (FIG. 3) may be provided to engage the gum (non-penetrating screws or pins) or teeth (e.g., blunt screws) or jaw bone (e.g. sharp screws). Alternative designs, for example as described below, may be used instead.

Figure 3:
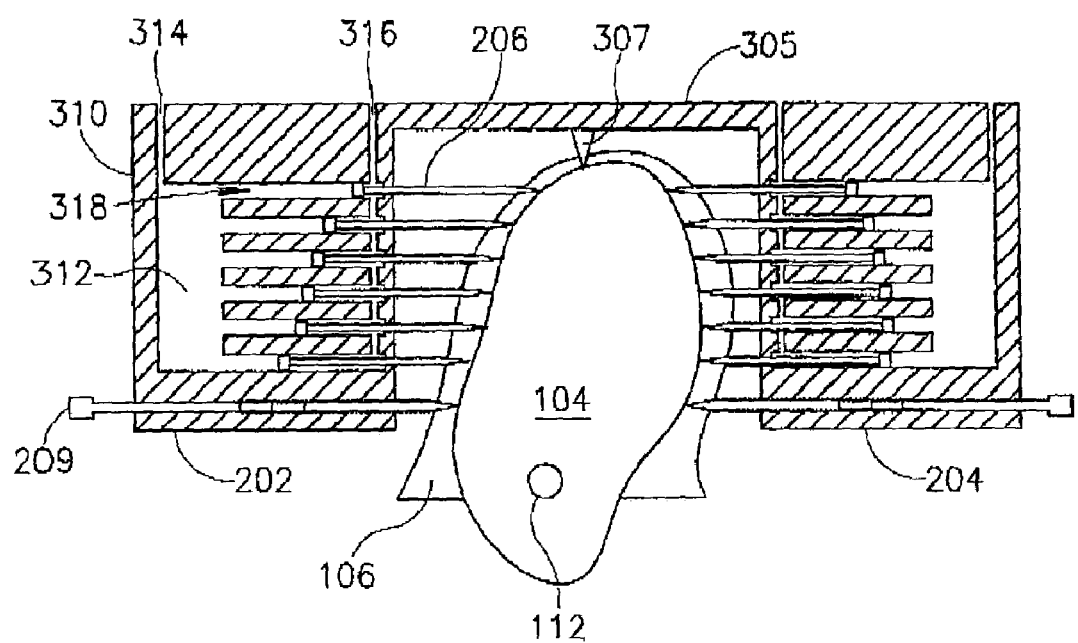
FIG. 3 is a schematic cross-sectional illustration of a mounted stent of FIG. 2.

FIG. 3 is a schematic cross-sectional illustration of a mounted stent 200, ignoring the drill guide. The pins 206 are shown penetrating soft tissue 106 and contacting bone 104. As the bone geometry is uneven, so is the penetration depth. In an exemplary embodiment of the invention, the tips define the surface and, if two panels are used, two sides of the bone are defined, as is the bone thickness (which varies, e.g., by the distance between the bone surfaces). As shown, each pin 206 has its own channel 318 in which it can axially advance or retract. All these channels are coupled via panel 202, providing a common reference for all the pins. Optionally, one or more inclined channels (not shown) are provided, for mapping of the upper part of bone 104, for example to determine how far the original tooth socket is resorted and the bone restructured. Alternatively or additionally, a top panel 305 with advancing pins 307 is provided for this purpose. Optionally (as shown), pins 307 are fixed in place, and are used, for example, to provide a known distance between the stent and the jaw bone from its top.

A housing 310 of stent 200 encloses the pins area and may be used, for example, for providing pressurized air for advancing and/or retracting of the pins. A channel (not shown) may be used to pass air pressure from one panel of the stent to the other. Alternatively or additionally, glue may be flowed into housing 310 (e.g., from an aperture not shown, using a syringe, for example) to lock the pins in place.

Operation of Measurement Element

Figure 4A:
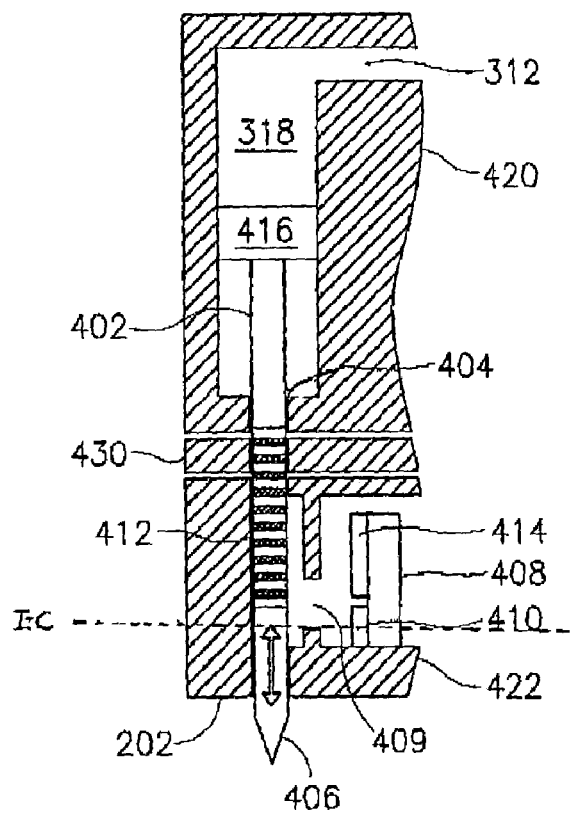
FIG. 4A is a schematic cross-section of a stent as in FIG. 2, showing the operation of a single pin, in accordance with an exemplary embodiment of the invention.
Figure 4B:
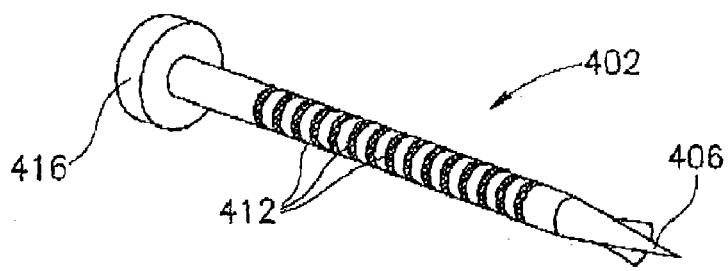
FIG. 4B is a schematic view of a single pin for the stent of FIG. 2.

FIG. 4A is a schematic cross-sectional illustration of a stent 200, showing the operation of a single pin 402, in accordance with an exemplary embodiment of the invention. FIG. 4B is a schematic illustration of pin 402, outside of a channel thereof 404. Pin 402 includes a tip 406, which is optionally sharp enough to penetrate soft tissue 106 without causing excessive pain and/or damage, while not being sharp enough to penetrate bone 104. Alternatively or additionally, tip 406 is otherwise adapted for preventing inadvertent bone penetration, for example, by providing one or more optional penetration stops (shown), or by shaping of the tip, such providing a stepped incline of tip 406, in some or all angular directions.

In an exemplary embodiment of the invention, the tip 406 is designed to work correctly and not penetrate bone under certain conditions, for example, under application of certain forces, such as smaller than 100, 50, 20 or 10 grams.

In an exemplary embodiment of the invention, an optical encoder 408 reads the relative and/or absolute position of pin 402, for example by detecting, using a detector 414, reflections of a LED source 410 from engraved or painted lines 412 of pin 402. Other marling methods may be used as well. Optionally, a pinhole aperature 409 is used to improve the detection. Alternatively, other methods and apparatus for determining the pin position, absolute and/or relative, optical and/or mechanical, can be used, for example as known in the art of translation detection and/or encoding. The precision of axial position determining can be, for example better than 1 mm, 0.5 mm or 0.2 mm, for example to within or better than the radiological image.

In an exemplary embodiment of the invention, pin 402 is advanced by pressing against a base 416 thereof, for example using air pressure. Referring also to FIG. 3, the plurality of pin channels 318 are interconnected to an optional volume 312 which is enclosed by housing 310. In an exemplary embodiment of the invention, air pressure is provided by an input vent 314. Any air that leaks around pins exits through an exit vent 316. Optionally, the operation of vents 314 and 316 can be exchanged, for example, by attaching a source to vent 316 and allowing 314 to be an exit vent. This exchanged operation is optionally used to retract pins 206.

In an exemplary embodiment of the invention, once pin 402 contacts jaw bone 104 it is locked in place, for example by shifting an apertured plate 430 in the plane the panel, so that the pins are frictionally engaged between plate 430 and channel 404. Alternatively or additionally, a ratchet mechanism is provided for each pin which allows only forward motion of the pin. Optionally, apertured plate 430 comprises inclined tabs (not shown) in its apertures which preferentially allows motion in one direction. Optionally, moving plate 430 releases tile ratchet. Alternatively, other methods and apparatus for locking pins in place may be used, for example as known in the art of locking. As will be noted below, for example, locking is not necessary in all embodiments of the invention.

In an exemplary embodiment of the invention, panel 202 (of which the figure shows only a small part) is formed of layers, a rigid channel layer 420, which guides pins 402, an optional PCB layer 422 on which the encoder is mounted and which provides data and power lines to the encoders and apertured locking plate 430 between the two layers. Mounting methods for electronics other than using a PCB, for example integrated optics, may be used instead.

Figure 4C:
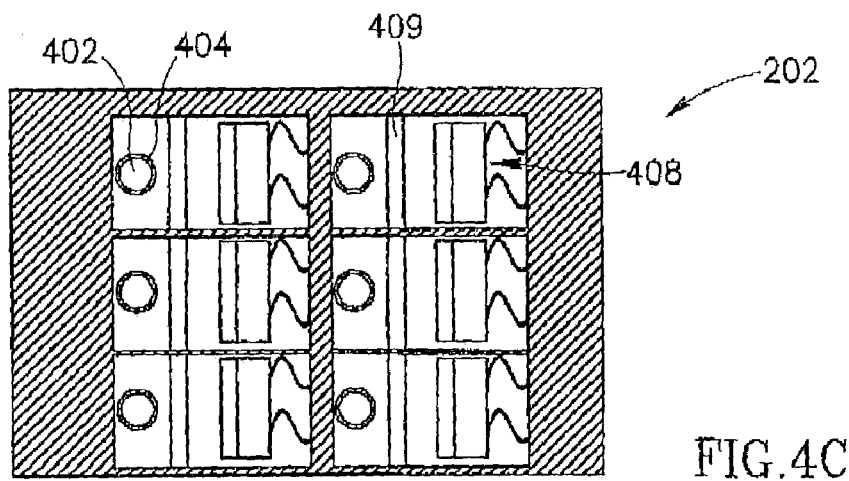
FIG. 4C is a top view of a part of a panel, showing the arrangement of a plurality of pins and their encoding circuitry, in accordance with an exemplary embodiment of the invention.

FIG. 4C is a cross-sectional view of a panel through line I-C on FIG. 4A, showing the arrangement of a plurality of pins and their encoding circuitry. In the exemplary embodiment shown, the pins are arranged in an array, with each pin having its own encoder. For example, each panel may include between 10 and 30 pins, arranged in a generally rectangular array. In an exemplary embodiment of the invention, each panel has 25 pins in a hexagonal arrangement. However, other arrangements, such as rectangular may be used. Also, smaller (e.g., 4) or greater (e.g., 30) numbers of pins per panel may be provided. An exemplary pitch is 2 mm between pins. Non-axial motion of the pins is desirably insubstantial, for example, limited to less than 10% or 5% of the pitch of the pins. It should be noted that in some embodiments of the invention, curved pins are used instead of straight pins.

In an exemplary embodiment of the invention, the stent dimensions are as follows: each panel has an active width (of pins, along the direction of the jaw) of between 5 and 12 mm. Each panel has an active height of 8–22 mm, for example 10 mm. The distance between the panels is for example, between 8 and 22 mm.

Design Details and Drill Guide

FIG. 5A is an exploded view of a stent 500 including a panel section 502, a panel section 504 and a drill guide section 506, in accordance with an exemplary embodiment of the invention. As shown, stent 500 comprises two locking plugs 508 and 509 which lock the panels to a drill guide base tube 510. Optionally, for example as described below, panel 502 may slide and lock at a variable and/or controllable distance from panel 504.

In an exemplary embodiment of the invention, plug 508 comprises electronics, for example for reading the encoders and/or for a wireless transmission link, such as BlueTooth. A battery or data and power cable are optionally included in plug 508, as needed. Optionally, plug 509 includes a pneumatic vent for attaching a standard dental air/water syringe for moving the pins, as described above. A semi-locked state (in which the pins do not move and substantially amount) is optionally achieved by maintaining the pneumatic pressure after pin insertion.

In an exemplary embodiment of the invention, drill guide 506 includes optical (or other) encoders to indicate the position and/or orientation of drill guide 506 and also optionally includes a locking mechanism (described below) for preventing motion of drill guide 506 once adjusted.

In an exemplary embodiment of the invention, drill guide 506 comprises a capsule 512, shown in top-cross-sectional view in FIG. 5B, which is positioned and oriented in base tube 510. In the design shown, three degrees of freedom are provided, axial motion along tube 510, and two degrees of rotation, namely rotation parallel to the axis or perpendicular to the axis of tube 510. Fewer or greater number of degrees of freedom can be provided instead. Two degrees of freedom are provided by capsule 512 sliding or rotating in tube 510. A third degree of freedom is provided by rotation of a sleeve 514 inside capsule 512. A locking screw and nut 516 and 518, and tab 520, are optionally used to lock the position and/or orientation of guide 506. Penetration depth into jaw bone is optionally set by selecting a suitable penetration stop 522. This depth is optionally measured on a CT image or by measuring an X-ray image. Alternatively or additionally, to selecting a stop 522 from a set of stops, stop 522 may be threaded to allow selectable depth by rotation. Alternatively or additionally, a telescopic stop 522 is used. Optionally, multiple stops 522 with different diameters are provided, for example to set different penetration depth for different stages of drilling with different diameter drill bits.

In an exemplary embodiment of the invention, drill guide 506 includes three position encoders 524, 526 and 528 which maybe all mounted on capsule 512 and connected by a cable 523 to other electronic components of stent 500. In an exemplary embodiment of the invention, encoder 524 reads horizontal markings 532 on the inside of tube 510; encoder 526 reads vertical markings 534 (shown dotted) on the inside of tube 510 and encoder 528 reads horizontal markings 536 on the outside of sleeve 514. Other encoder and marking configurations (or a mechanical or other type of encoder as known in the art) may be used instead. Optionally a cable 523 connects the encoders to electronics in stop 508 (or in another location).

Figure 5C:
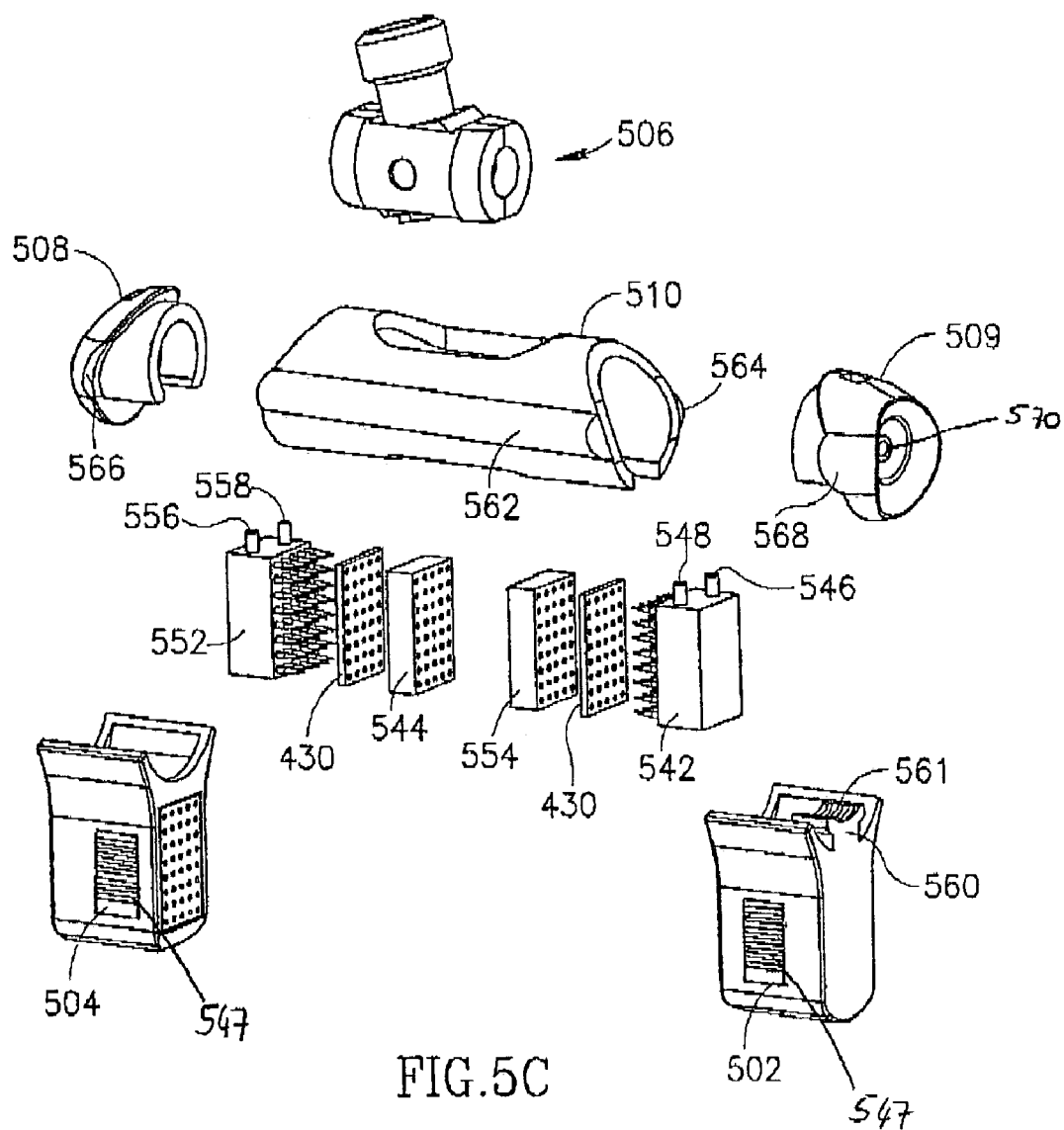

FIG. 5C shows another exploded view of stent 500 with some optional variations. The pin assemblies are shown as three packaged modules, a pneumatic package 542 (and 552), an optional apertured plate 430 and an electronic package 544 (and 554). In an exemplary embodiment of the invention, each package has an input vent 546 (and 556) and an output vent 548 (and 558). In the embodiment shown, a pair of tubes 562 and 564 are provided on base tube 510 to pass air pressure from one side of the stent to the other, with each tube connecting either the input or the output vents. Also shown are tube couplers 566 and 568 on the stops. Matching couplers, not shown are provided on the far side of the stops. Electronic wiring can, for example, pass in these tubes, or be printed or pasted on the inside or outside of tube 510. The electronic blocks 544 and 554 optionally include a multiplexer or data encoder of some type, to reduce the number of data lines needed. Optionally, manual switches 547 are provided for manual movement, locking and/or releasing of apertured plates 430. These switches may be, for example, self locking.

In an exemplary embodiment of the invention, panel 502 slides along tube 510 relative to panel 504. Optionally, a screw (not shown) is provided to set the distance between the panels. Alternatively or additionally, a sliding lock is used based on a close fit between a wing 560 and a slot cut in tube 510. If a force applied to panel 502 is not exactly parallel to the axis of tube 510, panel 502 rotates and wing 560 binds against tube 510. Optionally a position encoder (not shown) is provided, for example on capsule 512 or in stop 509, to read the panel position, for example by reading markings 561 of wing 560. In an alternative embodiment, no encoder is provided and the surface mapped by each panel is separately matched to a CT image. Optionally, this matching takes into account the type of offset allowed between the two panels.

In an exemplary embodiment of the invention, stent 500 is disposable. Alternatively it is sterilized between uses. Optionally, the division of the panels into packages allows easier sterilization. Alternatively or additionally, the electronics package, which may be more sensitive to sterilization is manufactured under very sterile conditions and/or sterilized using gas. This may reduce the cost of manufacturing.

Figure 5D:
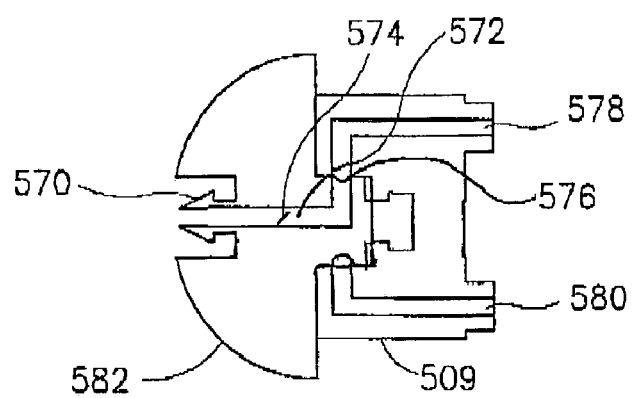

FIG. 5D is a cross-sectional view of stop 509 showing a pneumatic sub-system thereof. In an exemplary embodiment of the invention, a vent 570 is provided through which pressured air can be provided to a supply tube 572, for moving the pins. By rotating a housing section 582, an exit 576 of supply tube 572 is selectively attached to a first vent supply tube 578, attached to vents 558 and 548 or to a second vein supply tube 580 attached to vents 546 and 556. When supply tube 572 is not coupled to the vent supply tube, it optionally is open to the ambient air, to release pressure. A valve 574 is optionally provided to prevent pressure release through vent 570. Other pressure supply mechanisms can be used as well, for example, different tube selection mechanisms or using a separate vent 570 for each operation of advancing and retracting the pins.

Other designs for a drill guide may be used as well, for example ones in which the degrees of freedom are provided by a unitary mechanism, rather than one mechanism for each degree of freedom.

System and Usage

Figure 6:
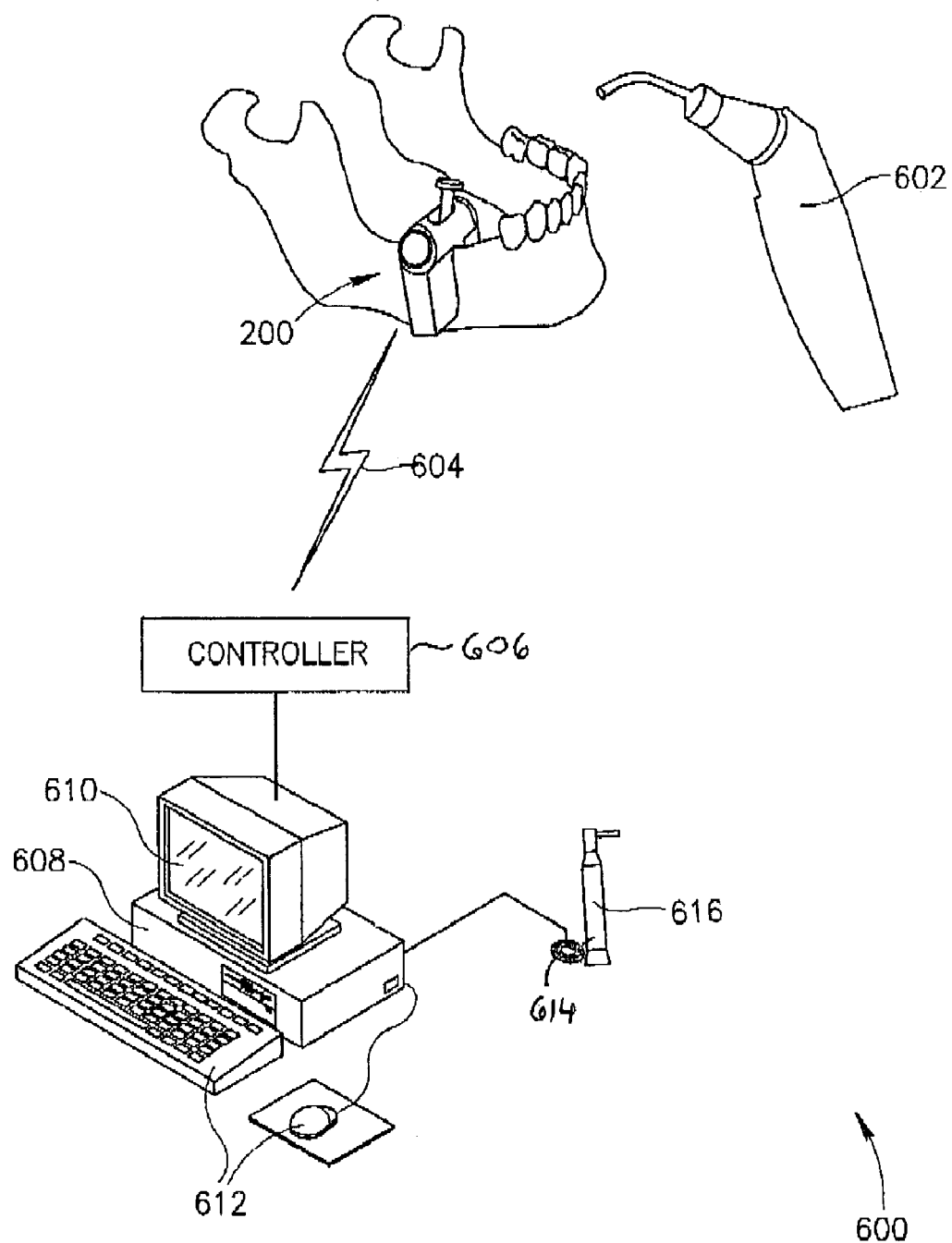
FIG. 6 is a schematic diagram showing a complete dental system including a stent, in accordance with an exemplary embodiment of the invention.

FIG. 6 is a schematic diagram showing a complete oral measurement system 600 including a stent 200, in accordance with an exemplary embodiment of the invention.

Stent 200 optionally includes a pneumatic pin advancing mechanism which is optionally powered by connection to a standard air pressure source 602. An RF data link 604 connects stent 200 to a controller 606 which receives information from the encoders. Alternatively or additionally, a cable connection is provided for the data and/or power. Optionally controller 606 is provided within the stent and connects directly to a standard or propriety interface on an external computer and/or provides on-stent indications for drilling directions. Alternatively, controller 606 is incorporated with or is attached to a computer 608, including a display 610 and a user input 612, which may be used for presenting surface geometry and/or for planning paths. Optionally, controller 606 and/or computer 608 is attached to one or more positioning sensors 614, for example of a type well known in the art, and adapted to attach to a drill 616 or the jaw. Such positioning sensors may be used to overlay the path of a dental tool on the 3D geometry and/or on a 3D or 2D radiological image shown on display 610, for example using methods well known in the art.

Figure 7A:
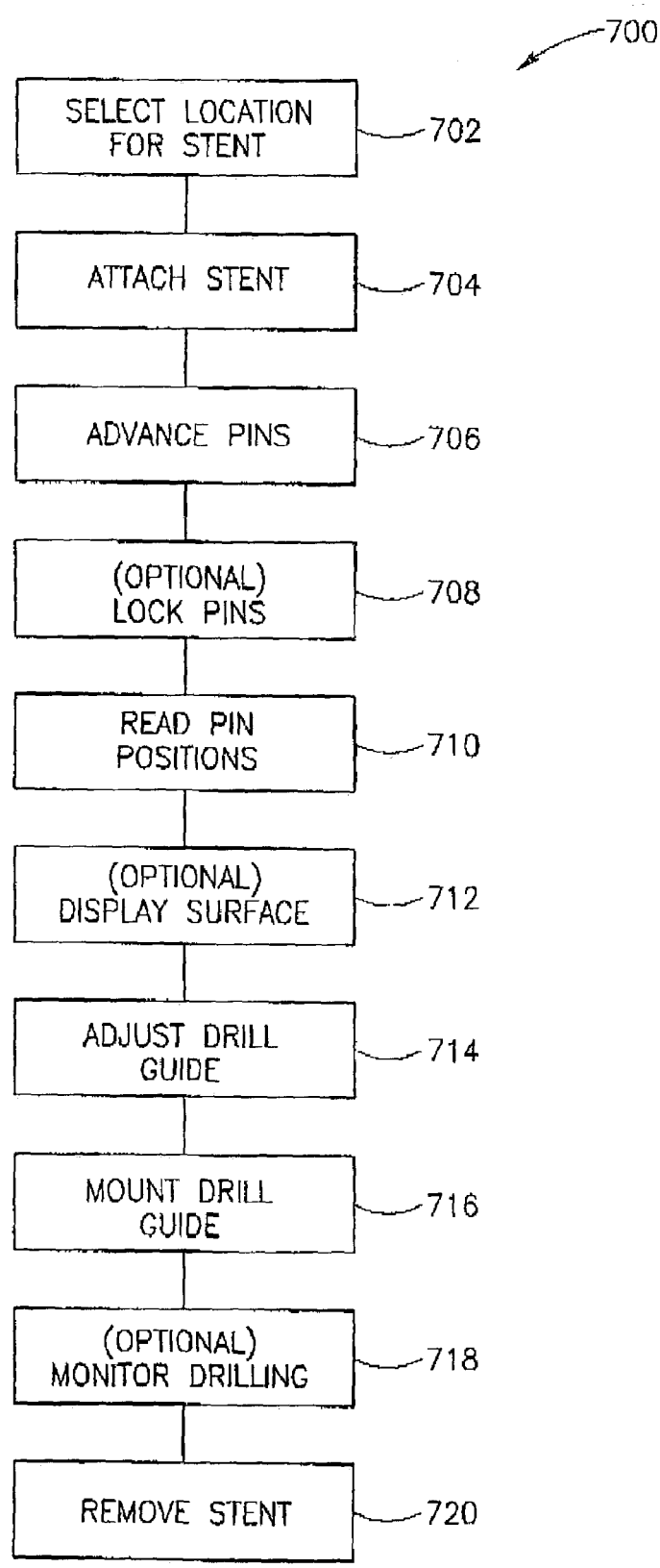
FIGS. 7A and 7B are flowcharts of the process of using a dental system as in FIG. 6, in accordance with an exemplary embodiment of the invention.

FIG. 7A is a flowchart 700 of the process of using a measurement system as in FIG. 6, in accordance with an exemplary embodiment of the invention.

At 702, a space 108 for implanting a tooth is identified and a suitably sized stent 200 is selected. In an exemplary embodiment of the invention, a relatively narrow stent is used and the implantation location position along the jaw is used to select the stent position, especially if the drill guide of the stent has no freedom of motion along the jaw. In some embodiments of the invention, a multiple drill-guide stent which optionally includes a template for drilling multiple holes, is provided.

At 704, the stent is optionally affixed to jaw 100, for example by advancing one or more blunt or sharp pins or screws. Alternatively, the advancing of pins 206 is used for locking to the jaw.

At 706, pins 206 are advanced, for example manually or using a pneumatic advancer.

At 708, the pins are optionally locked in place, for example mechanically or by gluing. It should be noted that in some embodiments of the invention, the pin position is only measured once and all the pin positions are sampled in parallel so no actual locking is required. Optionally, air pressure is used to keep the pins advanced to the bone.

At 710, the pin axial positions are read using the encoders and position data is optionally transferred to controller 606. Alternatively, for example as described in FIGS. 9 and 10, stent 200 is at least partially disassembled and read when it is off of jaw 100.

At 712, the bone geometry is optionally displayed on display 610 and a bore path and/or path limits are selected. Alternatively, for example as described in FIG. 7B, registration to a radiological image is carried out.

At 714, a drill guide is adjusted or fabricated (e.g., using an attached CAD/CAM system) to match these limitations. In an exemplary embodiment of the invention, the drill guide is manually adjusted until the encoders 524–528 show the desired values on display 610. Alternatively or additionally, a micro-motor set on stent 200 or in a separate jig are used to adjust the drill guide.

At 716, the drill guide is mounted on stent 200 (or it may be pre-mounted as shown above) and drilling is started. Optionally, a receptacle for the drill guide is provided on stent 200.

At 718, the drilling process is optionally monitored, for example by generating an audio or visual indication if the drill guide is outside of allowed parameters. Alternatively or additionally, the process is automatically stopped, for example using a power cut-off to the drill.

At 720, the stent is removed. Optionally, the pins are retracted or allowed to retract (e.g., having spring retraction), prior to stent removal. Alternatively or additionally, the two panel of the stent are pushed apart using a screw, so that the pins are forcefully retracted Alternatively or additionally, the panels are removed from stent 200. Alternatively or additionally, the stent includes a break line to be broken for removal.

Then, implantation can proceed using the drilled holes methods known in the art.

In an alternative embodiment of the invention, the drill guide (optionally with position/orientation encoders) is used on a different, standard, stent, for example, by providing a socket for it on a CAD/CAM manufactured surgical stent. Optionally, the surgical stent is manufactured with oversized drill guiding bores, if any, to allow Some freedom of selecting the bore using a drill guide according to the present invention.

In another alternative embodiment, the stent of the present invention is used in a procedure where gum tissue is peeled off, so the pins do not necessarily need to be designed to differentially penetrate hard tissue and soft tissue.

Stent Variations

Figure 8A:
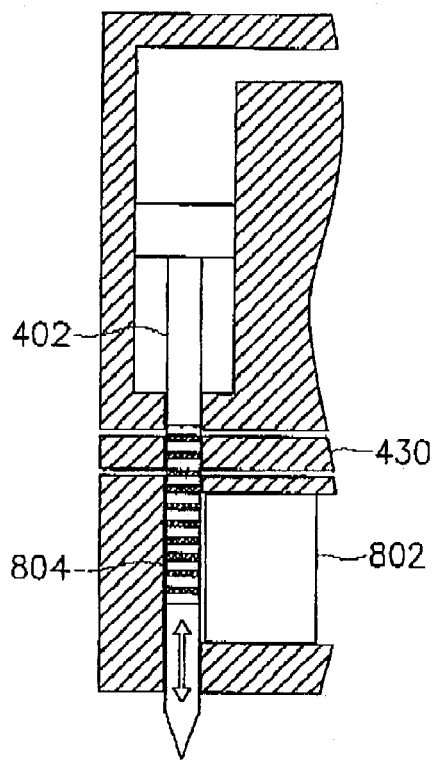
FIGS. 8A–8B show variations of pin mechanisms, in accordance with exemplary embodiments of the invention.
Figure 8B:
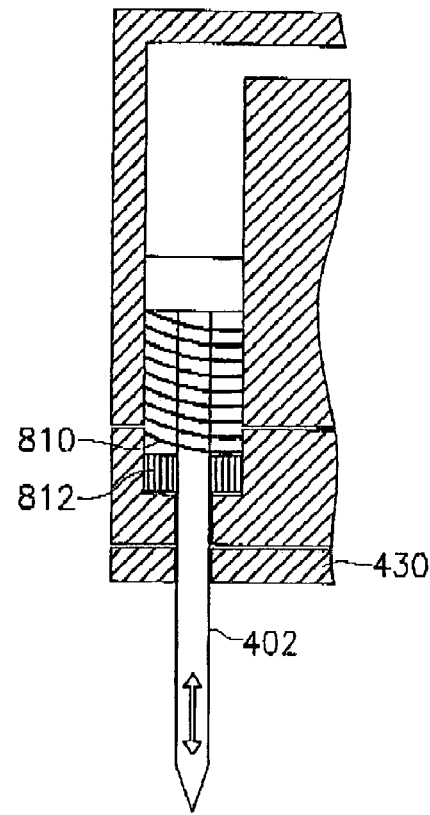

FIGS. 8A–8B show variations of pin mechanisms, in accordance with exemplary embodiments of the invention. In FIG. 8A, a non-optical position encoder 802 is used to read a position of pin 402. In one example, a resistive encoder is used, for example, if pin 402 is resistive. In another example, capacitance between encoder 802 and pin 402 is measured, using methods known in the art. In another example, encoder 802 senses a magnetic field put out by pin 402 and/or by markings (e.g., magnetic encoding) 804 thereon.

FIG. 8B shows an embodiment in which a spring 810 is used to advance or retract pin 402 (e.g., depending on the spring type). Air pressure may be used to maintain the spring in a compressed or stretched configurations. Pin position is determined, for example, by reading a pressure or strain sensor 812 coupled to spring 810. As noted above, locking of the pins may not be required, for example if the measurement time is short. In an alternative embodiment, a single encoder reads multiple pins, for example an imaging encoder can image the markings on multiple pins simultaneously.

In an exemplary embodiment of the invention, the pins are read in parallel. A multiplexer is optionally provided to place the signals on a relatively small number of data lines. Alternatively, the pins may be read in series.

Figure 8C:
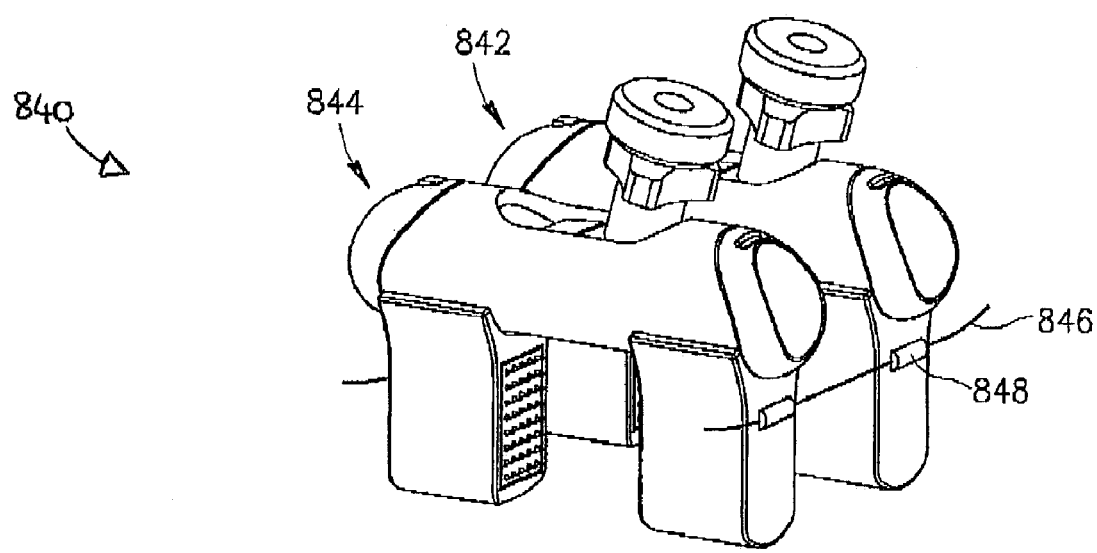
FIG. 8C shows a multi-tooth stent, in accordance with exemplary embodiments of the invention.

FIG. 8C shows a multi-tooth stent 840, in accordance with exemplary embodiments of the invention. When multiple teeth are to be implanted, often two or more holes are drilled and screws implanted. A rail may be attached to the screws and a multiple-tooth implant mounted on the rail. Stent 840 includes, for example, two stent portions 842 and 844, for example as described above, with a rigid or flexible attachment 846 (depending on the accuracy desired). Optional, an encoder 848 is provided for determining the distance between the stent portions. The electronics may all be provided on one of the stent portions. Optionally (not shown), one or both drill guides are movable (e.g., mounted on a rail, with optional position encoders) along the line connecting the two stent portions, for selecting of drill location. In an exemplary embodiment of the invention, such encoder input may be used to assist the surface matching (described below) by providing a starting point.

In general, if a stent is not mounted in a correction location, it may be removed and re-inserted. Alternatively, the stent may be wide enough to allow movement of the drill guide. In any case, by viewing the CT image, it can be seen if the current bore direction clashes with existing roots or otherwise is unsuitable.

Registration Variations

Figure 7B:
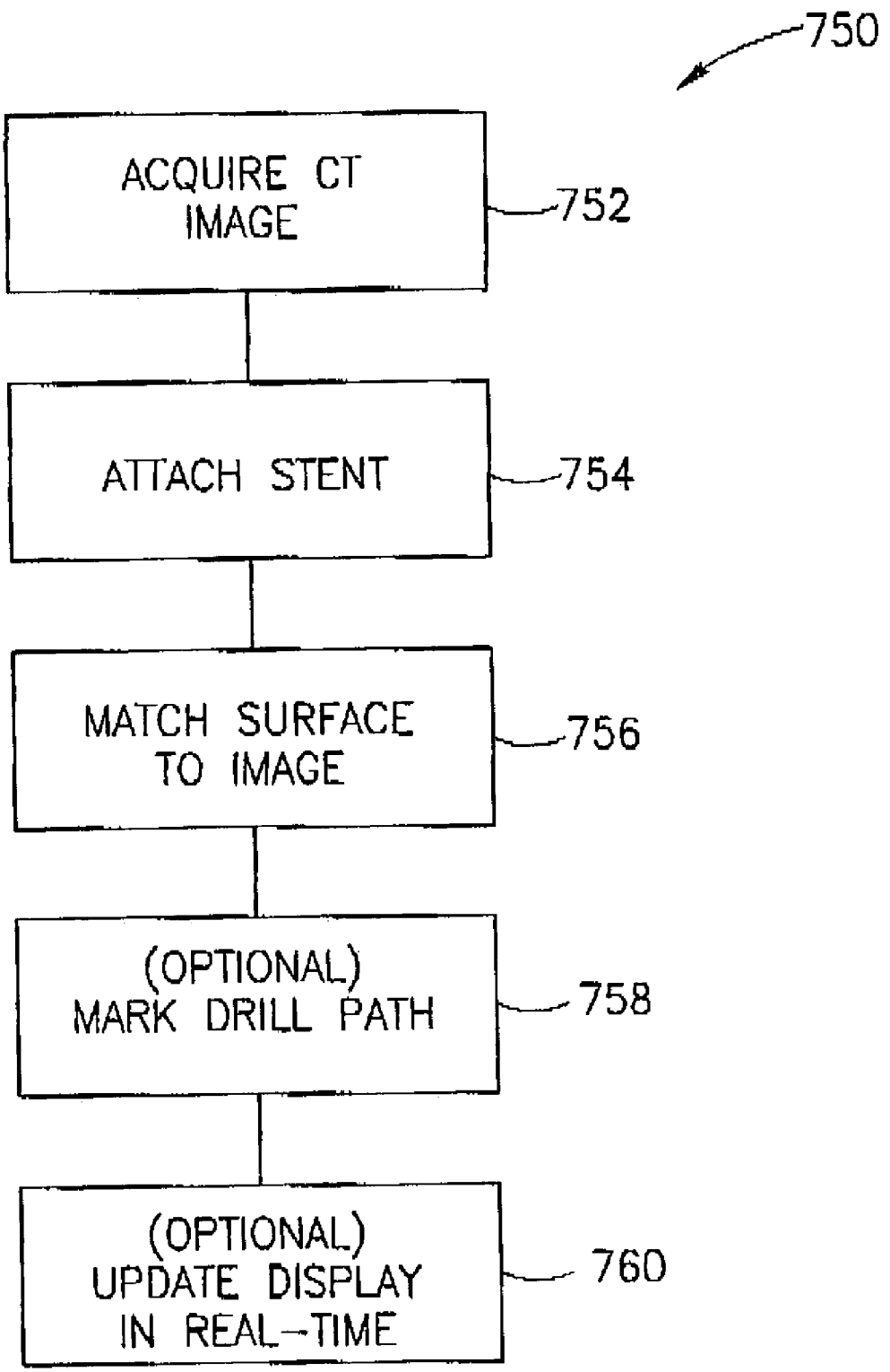

FIG. 7B is a flowchart 750 of a process for registering stent 200 to a previously acquired CT image.

At 752, a CT image (or other 3D radiological image) of the jaw is acquired.

At 754, a stent 200 is attached, as described above.

At 756, the surface data received from stent 200 is matched to a surface contour on the CT image, so that the stent and CT image are registered. Various matching methods can be used, for example using a segmentation algorithm to determine the surface contours on the CT image and then doing a maximum likelihood match for the two contours. Optionally the user indicates an initial approximate registration point. Other matching methods, for example based on correlation or landmarks, may be used.

At 758, drill paths are optionally marked on the display and registered to the stent and various drill path selection methods may be applied.

At 760, the display is optionally updated in real time, for example showing device positions based on a position sensor and/or showing drill path based on input from the stent encoders 524–528.

Disassembled Stent

Figure 9:
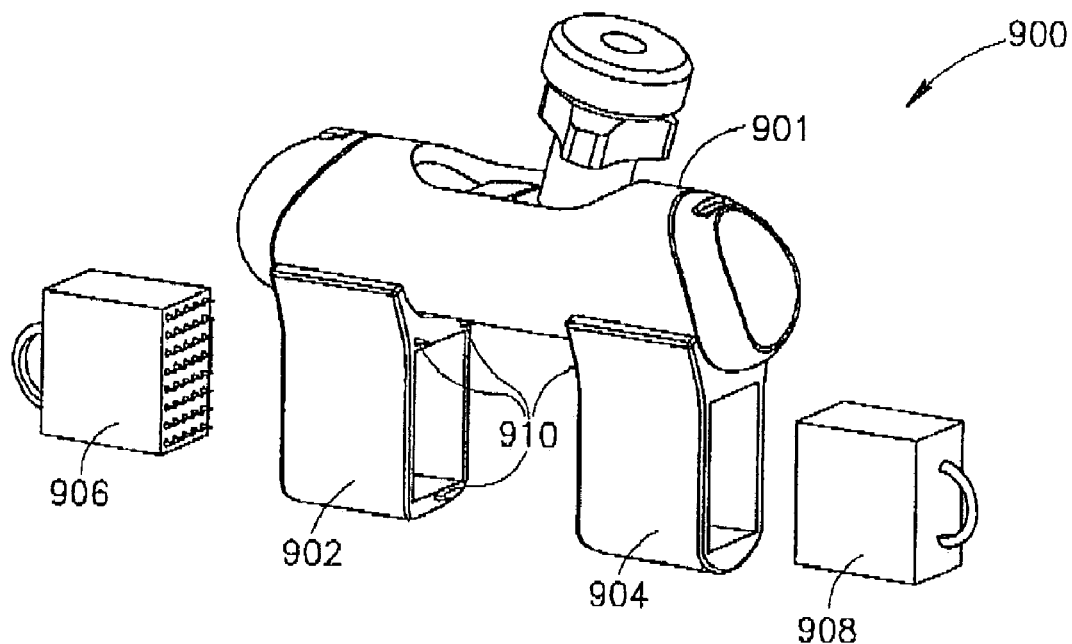
FIG. 9 is a schematic illustration of a stent designed for disassembly, in accordance with an exemplary embodiment of the invention.
Figure 10:
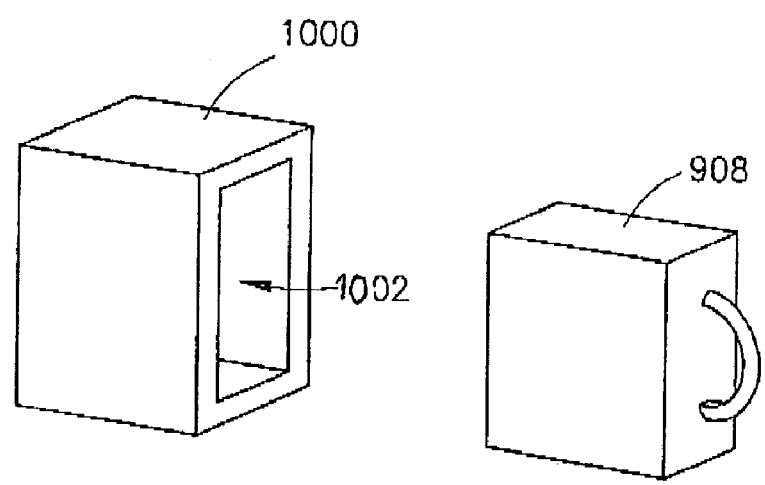
FIG. 10 is a schematic illustration of an exemplary stent reader for the stent of FIG. 9.

FIG. 9 is a schematic illustration of a stent 900 designed for disassembly, in accordance with an exemplary embodiment of the invention. Stent 900 comprises a stent body 901 having two panel portions 902 and 904, each defining a receptacle 907 for a pin package 906 and 908. Pneumatic couplers (not shown) are optionally provided on the tops of the pin packages.

During usage, the pins are advanced and the locked in place. The pin packages are then removed and read using an external reader 1000, as shown for example in FIG. 10. In an exemplary embodiment of the invention, reader 1000 includes (inside a receptacle 1002 thereof) a plurality of position encoders (or one or more array imagers) which detect the tip location. Alternatively, the whole stunt is mounted on such an external reader. Alternatively, the backs of pin packages 906 and 908 are opened and the bases of the pins read. Alternatively or additionally, reader 1000 includes electronics for reading and/or powering encoders provided in the packages.

In an exemplary embodiment of the invention, the pins are spring loaded to advance and are forced towards the bone until they are pushed back from the bone. Glue or another other locking mechanism is used to lock the pins in place. In an exemplary embodiment of the invention, the pin-packages are pre-filled with a glue that sets shortly after the package is exposed to ambient air.

Optionally, one or more fixed pins 910 is provided for locking stent 900 to the jaw, by advancing panels 902 and 904 towards each other.

It will be appreciated that the above described methods of bone surface measurement may be varied in many ways, including, changing the order of steps and the types of tools used. In addition, a multiplicity of various features, both of method and of devices have been described. In some embodiments mainly methods are described, however, also apparatus adapted for performing the methods are considered to be within the scope of the invention. It should be appreciated that different features may be combined in different ways. In particular, not all the features shown above in a particular embodiment are necessary in every similar embodiment of the invention. Further, combinations of the above features are also considered to be within the scope of some embodiments of the invention. Also within the scope of the invention are surgical kits which include sets of medical devices suitable for performing a single or a small number of measurements. Also, within the scope is software and computer readable-media including such software which is used for carrying out and/or guiding the steps described herein, such as surface matching and bore selection. When used in the following claims, the terms "comprises", "includes", "have" and their conjugates mean "including but not limited to".

It will be appreciated by a person skilled in the art that the present invention is not limited by what has thus far been described. Rather, the scope of the present invention is limited only by the following claims.

What is claimed is:

1. Apparatus for measuring a surface geometry of hard tissue covered by a layer of soft tissue, comprising:
   (a) a plurality of elements each having a tip adapted to penetrate said soft tissue and not substantially penetrate said hard tissue;
   (b) a frame supporting movement of said elements, each along a path, such that a plurality of said tips, when positioned along the paths, define a surface of the hard tissue, such that not all the tips lie in a same plane;
   (c) at least one position sensor which generates a signal indicative of a tip position of at least one of said elements; and
   (d) at least one support adapted to lock said frame relative to one or both of said soft tissue and said hard tissue.

2. Apparatus according to claim 1, wherein each said path comprises a path along an axis of an elements.

3. Apparatus according to claim 1, wherein said elements are elongate.

4. Apparatus according to claim 1, wherein said frame comprises two substantially oppositely facing panels, each of which panels supports a plurality of said elements.

5. Apparatus according to claim 4, wherein said frame comprises at least one upper panel supporting a plurality of said elements.

6. Apparatus according to claim 4, wherein said frame comprises at least one upper panel supporting at least one fixed soft tissue penetration element.

7. Apparatus according to claim 4, wherein said tips are adapted to measure at least three sides of a shape generally corresponding to a rectangle, while mounted in said frame.

8. Apparatus according to claim 4, wherein said elements are arranged as a first set perpendicular to one plane, a second set generally facing said first set and a third set oblique to said first and second sets.

9. Apparatus according to claim 1, wherein at least some of said plurality of elements are arranged in two dimensions, with at least three elements in each of two orthogonal directions.

10. Apparatus according to claim 1, wherein said frame is adapted for disassembly.

11. Apparatus according to claim 1, wherein said plurality of elements comprises at least 10 elements.

12. Apparatus according to claim 1, wherein said plurality of elements comprises at least 30 elements.

13. Apparatus according to claim 1, sized and having a geometry adapted for a dental application of measuring a surface of a jaw bone based on axial positions of said tips.

14. Apparatus according to claim 1, wherein said hard tissue comprises cortical bone tissue.

15. Apparatus according to claim 1, wherein said tips have a density of at least one tip per nine square millimeters.

16. Apparatus according to claim 1, wherein said tips have a density of at least one tip per square millimeter.

17. Apparatus according to claim 1, wherein said frame substantially allows only motion of each of said elements, along an axis of the element.

18. Apparatus according to claim 17, wherein said frame is limited to non-axial motion to within a tolerance of less than 10% of a pitch of said elements.

19. Apparatus according to claim 18, wherein said frame allows only axial motion of said elements, within a tolerance of less than 5% of a pitch of said elements to non-axial motion of said tips.

20. Apparatus according to claim 1, wherein said tips are made sharp enough to penetrate soft tissue but not so sharp that they penetrate cortical bone under an application force of under 50 grams per tip.

21. Apparatus according to claim 1, wherein said tips include a bone stop which prevents entry of the elements into bone tissue past a predetermined distance.

22. Apparatus according to claim 1, wherein said at least one position sensor comprises a single encoder common to multiple elements.

23. Apparatus according to claim 22, wherein said at least one position sensor comprises an imaging sensor.

24. Apparatus according to claim 1, wherein said at least one position sensor comprises at least one encoder per element.

25. Apparatus according to claim 24, wherein said at least one encoder comprises an optical encoder reading a position marking off of an element.

26. Apparatus according to claim 24, wherein said at least one encoder comprises a magnetic encoder reading a position marking off of an element.

27. Apparatus according to claim 24, wherein said at least one encoder comprises a resistance encoder reading a resistance of an element.

28. Apparatus according to claim 24, wherein said at least one encoder comprises a capacitance encoder reading a capacitance of an element.

29. Apparatus according to claim 24, wherein said at least one encoder comprises a force encoder reading a compression of a spring attached to an element.

30. Apparatus according to claim 1, wherein said at least one position sensor has a precision of better than 0.5 mm.

31. Apparatus according to claim 1, wherein said at least one position sensor has a precision of better than 0.2 mm.

32. Apparatus according to claim 1, wherein said at least one position sensor is integral to said frame.

33. Apparatus according to claim 1, wherein said at least one position sensor is separate from said frame.

34. Apparatus according to claim 33, comprising a holder for at least part of said frame in which said at least one position sensor is integrated.

35. Apparatus according to claim 1, comprising an element advance mechanism operative to simultaneously advance a plurality of said elements through said soft tissue at a same time.

36. Apparatus according to claim 35, wherein said element advance mechanism is adapted to apply a force limited to prevent inadvertent penetration of said hard tissue.

37. Apparatus according to claim 35, wherein said element advance mechanism comprises a pneumatic advance mechanism.

38. Apparatus according to claim 37, comprising a pneumatic channel for each of said elements.

39. Apparatus according to claim 37, wherein said advance mechanism is operable as an element retractor.

40. Apparatus according claim 1, comprising at least one position lock for at least one of said elements.

41. Apparatus according to claim 40, wherein said position lock comprises a friction lock defined by a panel perpendicular to an axial motion direction of said elements.

42. Apparatus according to claim 1, comprising a source of adhesive adapted to provide adhesive to lock said elements to said frame.

43. Apparatus according to claim 1, comprising a drill guide.

44. Apparatus according to claim 43, wherein said drill guide is adapted to guide a standard dental drill bit.

45. Apparatus according to claim 44, wherein said drill guide is adapted to limit a depth of penetration of said drill bit.

46. Apparatus according to claim 44, wherein said drill guide comprises at least one penetration limitation sleeve having a selectable offset from said frame.

47. Apparatus according to claim 46, wherein said at least one penetration limitation sleeve comprises a plurality of sleeves each having a different offset.

48. Apparatus according to claim 43, wherein said drill guide is locked to said frame.

49. Apparatus according to claim 48, wherein said drill guide is adjustable in at least two degrees of freedom of position and orientation prior to being locked to said frame.

50. Apparatus according to claim 49, comprising at least one encoder adapted to measure at least one of said degrees of freedom.

51. Apparatus according to claim 48, wherein said drill guide is adjustable in at least three degrees of freedom of position and orientation prior to being locked to said frame.

52. Apparatus according to claim 1, wherein said at least one position sensor comprises a data output.

53. Apparatus according to claim 52, wherein said data output is wireless.

54. Apparatus according to claim 52, comprising a three-dimensional display system to which said data output is attached, which display system is adapted to display an indication of said surface.

55. Apparatus according to claim 54, wherein said display system overlays said surface on a three dimensional representation of said hard tissue.

56. Apparatus according to claim 55, and including a controller configured to register said surface to said representation.

57. Apparatus according to claim 54, wherein said display system generates alerts responsive to an undesirable spatial position of a tool relative to said surface.

58. Apparatus according to claim 54, wherein said display system generates an indication of at least one of a position and orientation of a drill guide mounted on said frame.

59. Apparatus recording to claim 58, wherein said indication comprises indication of a projected drill bore.

60. Apparatus according to claim 52, comprising a computerized manufacturing system to which said data output is attached, for manufacture of a drill guide for said hard tissue.

61. Apparatus according to claim 1, comprising a plurality of elements having tips adapted to not penetrate soft tissue.

62. A method of measuring the surface of a hard tissue underlying a soft tissue, comprising:
   (a) inserting a plurality of different sharp elements through said soft tissue to a surface of said hard tissue;
   (b) determining at least relative positions of tips of said sharp elements;
   (c) reconstructing a map of said surface of said hard tissue from said at least relative positions; and
   (d) providing said elements mechanically coupled to a frame and locking said frame to at least one of said hard tissue and said soft tissue, prior to said inserting such that motion of said elements is limited to axial motion.

63. A method according to claim 62, comprising using said map to guide a drill to said hard tissue.

64. A method according to claim 63, comprising providing a drill guide for using said map.

65. A method according to claim 64, wherein said hard tissue comprises a jaw bone and wherein said soft tissue comprises gum tissue.

66. A method according to claim 64, comprising selecting an offset sleeve for controlling a depth of said drilling.

67. A method according to claim 64, comprising adjusting said drill guide according to said map.

68. A method according to claim 64, wherein said elements are mounted on two opposing panels of a frame and comprising approximating said panels.

69. A method according to claim 64, comprising registering said map to a previously acquired radiological image of said hard tissue.

70. A method according to claim 64, comprising providing real-time feedback on at least one of a position and orientation of said drill guide.

71. A method according to claim 62, wherein inserting comprises inserting using a standard dental pneumatic source.

72. A method according to claim 62, comprising removing said elements using a standard dental pneumatic source.

73. A method according to claim 62, comprising removing said elements from said soft tissue prior to said determining.

74. A method according to claim 62, comprising removing said elements from said soft tissue after said determining.

75. A method according to claim 62, comprising locking said elements prior to said determining.

76. A method according to claim 62, comprising not locking said elements prior to said determining.

77. Apparatus for measuring a surface geometry of hard tissue covered by a layer of soft tissue, comprising:
- (a) a plurality of elements each having a tip adapted to penetrate said soft tissue and not substantially penetrate said hard tissue;
- (b) a frame supporting movement of said elements, each along a path, such that a plurality of said tips, when positioned along the paths, define a surface of the hard tissue, such that not all the tips lie in a same plane; and
- (c) at least one position sensor which generates a signal indicative of a tip position of at least one of said elements, wherein at least some of said plurality of elements are arranged in two dimensions, with at least three elements in each of two orthogonal directions.

78. Apparatus for measuring a surface geometry of hard tissue covered by a layer of soft tissue, comprising:
- (a) a plurality of elements each having a tip adapted to penetrate said soft tissue and not substantially penetrate said hard tissue;
- (b) a frame supporting movement of said elements, each along a path, such that a plurality of said tips, when positioned along the paths, define a surface of the hard tissue, such that not all the tips lie in a same plane; and
- (c) at least one position sensor which generates a signal indicative of a tip position of at least one of said elements, wherein said frame comprises two substantially oppositely facing panels, each of which panels supports a plurality of said elements.

79. Apparatus for measuring a surface geometry of hard tissue covered by a layer of soft tissue, comprising:
- (a) a plurality of elements each having a tip adapted to penetrate said soft tissue and not substantially penetrate said hard tissue;
- (b) a frame supporting movement of said elements, each along a path, such that a plurality of said tips, when positioned along the paths, define a surface of the hard tissue, such that not all the tips lie in a same plane; and
- (c) at least one position sensor which generates a signal indicative of a tip position of at least one of said elements, wherein said tips include a bone stop which prevents entry of the elements into bone tissue past a predetermined distance.

80. Apparatus for measuring a surface geometry of hard tissue covered by a layer of soft tissue, comprising:
- (a) a plurality of elements each having a tip adapted to penetrate said soft tissue and not substantially penetrate said hard tissue;
- (b) a frame supporting movement of said elements, each along a path, such that a plurality of said tips, when positioned along the paths, define a surface of the hard tissue, such that not all the tips lie in a same plane;
- (c) at least one position sensor which generates a signal indicative of a tip position of at least one of said elements; and
- (d) an element advance mechanism operative to simultaneously advance a plurality of said elements through said soft tissue at a same time.

81. Apparatus for measuring a surface geometry of hard tissue covered by a layer of soft tissue, comprising:
- (a) a plurality of elements each having a tip adapted to penetrate said soft tissue and not substantially penetrate said hard tissue;
- (b) a frame supporting movement of said elements, each along a path, such that a plurality of said tips, when positioned along the paths, define a surface of the hard tissue, such that not all the tips lie in a same plane;
- (c) at least one position sensor which generates a signal indicative of a tip position of at least one of said elements; and
- (d) a drill guide locked to said frame.

* * * * *